United States Patent [19]

Chmiel et al.

[11] Patent Number: 5,393,538
[45] Date of Patent: Feb. 28, 1995

[54] PREPARATION OF CRUMB-FLAVORED MILK CHOCOLATE

[75] Inventors: Oliver Chmiel; Eric Raetz, both of Lausanne; Helmut Traitler, Corseaux, all of Switzerland

[73] Assignee: Nestec S.A., Vevey, Switzerland

[21] Appl. No.: 43,656

[22] Filed: Apr. 6, 1993

[30] Foreign Application Priority Data

Apr. 25, 1992 [EP] European Pat. Off. ............ 92107095

[51] Int. Cl.⁶ ............................................. A23G 1/00
[52] U.S. Cl. ........................................ 426/35; 426/42; 426/588; 426/660
[58] Field of Search ...................... 426/593, 35, 42, 44, 426/45, 584, 650, 655, 660, 588

[56] References Cited

U.S. PATENT DOCUMENTS

| | | |
|---|---|---|
| 1,966,460 | 7/1934 | Otting . |
| 2,169,278 | 8/1939 | Otting . |
| 2,835,593 | 5/1958 | Rusoff .................. 426/35 |
| 3,469,993 | 9/1969 | Pangier ................. 426/35 |
| 3,477,853 | 11/1969 | Hull ...................... 426/35 |
| 4,065,580 | 12/1977 | Feldman et al. . |
| 4,081,568 | 3/1978 | Bracco . |
| 4,084,011 | 4/1978 | Chevalley ............ 426/584 |
| 4,275,081 | 6/1981 | Coleman .............. 426/35 |
| 5,108,916 | 4/1992 | Cobbs et al. . |
| 5,114,734 | 5/1992 | Kibler ................... 426/650 |

FOREIGN PATENT DOCUMENTS

| | | |
|---|---|---|
| 0948022 | 5/1974 | Canada ................. 426/660 |
| 0149520 | 7/1985 | European Pat. Off. . |
| 3739700 | 6/1989 | Germany . |
| 524466 | 8/1940 | United Kingdom . |
| 1174854 | 12/1969 | United Kingdom . |
| WO8902916 | 4/1989 | WIPO . |
| WO9000016 | 1/1990 | WIPO . |
| WO9013638 | 11/1990 | WIPO . |

OTHER PUBLICATIONS

Database WPIL Derwent Publications Ltd. AN 85-156198 (1985).
Huge-Jensen, et al., "Studies on Free and Immobilized Lipases From Mucor michei", JAOCS, vol. 65, No. 6 (1988).
Jensen, et al., "Selectivity is an Important Characteristic of Lipases (Acylglycerol Hydrolases)" Biocatalysis, vol. 3, pp. 307–316 (1990).
Johri, et al., "Lipase From Sporotrichum (Chrysosporium) Thermophile Apinis: Production and Characteristics of Free and Immobilized Enzyme", J. Microb. Biotechnol., vol. 6(2), pp. 44–57 (1991).
Makiko, et al., Patent Abstracts of Japan, JP-A-62201576 (1987).
Fumikazu, Patent Abstracts of Japan, JP-A-63000274 (1988).
Yoshiko, et al., Patent Abstracts of Japan JP-A-63233750 (1988).
Hideaki, et al., Patent Abstracts of Japan JP-A-2242643 (1990).
Toyama Chem. KK, Database WPIL Derwent Publications Ltd., AN 90-174669 (1990).
Ranny, et al., "Synthetische Phosphoglyceride, 1. Mitt." Tensice Detergents, vol. 13, No. 2, (1976) (and partial translation), pp. 77–82.
Van Nievwenhuyzen, "The Industrial Uses of Special Lecithins: A Review." J. of the Amer. Oil Chem., vol. 58, No. 2, (1988) pp. 886–888.
Bonekamp-Nasner, "Emulsifiers–Lecithin and Lecithin Derivatives in Chocolate." Confectionery Production, vol. 58 No. 1, (1992). pp. 66 and 68.

*Primary Examiner*—Carolyn Paden
*Attorney, Agent, or Firm*—Vogt & O'Donnell

[57] ABSTRACT

A crumb-flavored milk composition is prepared by incorporating free fatty acids selected from the group consisting of oleic acid, linoleic acid and α-linolenic acid, or by incorporating a lysolecithin lysate or a milk treated with a modified lipase which preferentially releases unsaturated long-chain fatty acids.

9 Claims, No Drawings

PREPARATION OF CRUMB-FLAVORED MILK CHOCOLATE

BACKGROUND OF THE INVENTION

This invention relates to the flavouring of a milk chocolate.

Milk chocolate is made from a crude chocolate mixture consisting of cocoa powder, cocoa butter, milk and sugar. This mixture is finely ground and the resulting powder is refined and then liquefied by mixing in conches. The liquid chocolate is then tempered and moulded.

In one particular process used at present, which produces a milk chocolate with a caramel, fruity and milky flavour very popular among consumers, the crude chocolate mixture consists of "crumb", sugar and cocoa butter. The crumb is prepared by heat treatment of milk, addition of sugar, concentration in vacuo, mixing of the sweetened concentrated milk and the cocoa and complete drying of the resulting mixture in vacuo, i.e. to a residual moisture content of at most 1.5% by weight. The crumb is in the form of a dark hard mass which is finely ground, introduced into moisture-proof bags and then stored in a dry conditioned atmosphere. This mass keeps for a long time and develops a typical crumb flavour with, in addition, a milky note after several months' storage produced by enzymatic autolipolysis.

According to U.S. Pat. No. 4,081,568, lipolysis can be accelerated and made more constant by adjusting the pH of the crude chocolate mixture to a value of 6.25 to 6.7 by addition of trisodium phosphate before drying.

According to Great Britain Patent Specification 524,466, the butyric note in a fat for flavouring milk chocolate is accentuated by lipolysis of cream by a non-specific lipase followed by separation of the fatty phase which is used as flavouring agent for incorporation in the cocoa butter during production of the chocolate.

Accordingly, it has hitherto been accepted that the elements responsible for flavouring, particularly those formed during ripening of the crumb, were essentially the short chain fatty acids.

SUMMARY OF THE INVENTION

Applicants have surprisingly found a way of providing milk chocolate with a flavour close to that of the crumb without having to resort to the complicated and expensive production and ripening of the crumb.

Accordingly, the present invention relates to a process for flavouring milk chocolate, in which the milk chocolate is conventionally produced from milk powder, sugar, cocoa butter and lecithin, characterized in that a quantity of free fatty acid selected from oleic acid, linoleic acid and alpha-linolenic acid sufficient to provide the chocolate with a particular flavour close to that obtained from the crumb is added during the production process or is produced by lipolysis of a substrate involved in the production process.

According to the invention, the free unsaturated fatty acids mentioned above may be added in the solid state by simple mixing with the milk powder at a temperature below the melting point of the fatty acids. The quantity of fatty acid used is preferably from 0.4 to 1.2% by weight.

Alternatively, the free unsaturated fatty acids mentioned above may be produced by lipolysis of a substrate which is a constituent element of the mixture forming the chocolate paste. By this is meant the powdered milk—either whole or skimmed to a greater or lesser extent, for example containing approximately 4 to 26% fats—or the lecithin.

Thus, the milk powder may be lipolyzed with a specific lipase which preferentially orients lipolysis towards the production of long-chain unsaturated fatty acids and which is the subject of applicants' European Patent Application EP 92107094.2 filed under the title "A modified lipase, a process for modifying a lipase and the use of the lipase thus modified".

In one preferred form of the embodiment comprising lipolysis of a substrate, lecithin, for example soya lecithin, is subjected to lysis by a phospholipase A2, the phospholipase is then destroyed by a non-chemical treatment, for example by the action of a protease, and the protease is inactivated. The lysolecithin may be used to replace 20 to 70% by weight of the lecithin normally added in the conventional process either in the starting mixture or at the conching stage. In this connection, it is entirely surprising that the lecithin is suitable as a flavouring agent because, hitherto, it has been considered to be responsible for the formation of undesirable bad odours. In addition, it has hitherto been accepted in the field of chocolate production that the lecithin solely performed a physicochemical function of reducing the viscosity of the cocoa paste.

EXAMPLES

The process according to the invention is illustrated by the following Examples in which parts and percentages are by weight, unless otherwise indicated.

Standard Comparison Product

A milk chocolate is conventionally produced as follows:

46.5% sugar, 6.5% cocoa powder containing 12% cocoa butter, 18.5% cocoa butter, 22% whole milk powder containing 26% fats and 1% butter oil (the percentages are based on the final mixture after conching) are mixed. After refining and conching for 24 hours, during which the mixture is completed with 5.2% cocoa butter and 0.3% lecithin, the liquid chocolate is poured into moulds, the chocolate is demoulded and then stored at 15° C. This chocolate forms the standard comparison product.

A known method for flavouring a milk powder in which milk is subjected to lipolysis before introduction into the preceding mixture is used by way of comparison. To this end, the milk is treated with 0.02 U/ml lipase of *Mucor javanicus* (MAP-10, AMANO) for 30 minutes at 37° C. and is then dried by spray drying. The milk powder thus lipolyzed is used in the production of a milk chocolate as described above.

EXAMPLES 1–6

Example 1

0.0225% oleic acid and 0.02% linoleic acid are mixed with the milk powder in a chamber at −40° C. and the powder obtained is used as described above.

Example 2

0.05% oleic acid, 0.05% linoleic acid and 0.01% alpha-linolenic acid are mixed with the milk powder in a chamber at −40° C. and the powder obtained is used as described above.

Example 3

2 g soya lecithin are treated with 4 ml of a solution of phospholipase A2 (LECITHASE ®, NOVO), activity 10,000 U/ml, in an aqueous medium of which the pH has been adjusted to 9 by addition of 4M sodium hydroxide, after which calcium chloride is added to obtain a concentration of 0.4M in the solution. The solution is then incubated with stirring for 2 h at 55° C. 4 ml ALCALASE 2,4L (NOVO, 2.4 activity units/g) are then added and the mixture is stirred for 1 hour at 50° C. to inactivate the phospholipase. Finally, the mixture is heated to 75° C. and is stirred at that temperature for 15 minutes to destroy the proteolytic activity of the protease. The lysate obtained is used to replace 30% of the lecithin used in the production of chocolate as described above.

Example 4

The procedure is as in Example 3, except that the lysate is used to replace 60% of the lecithin used in the production of chocolate as described above.

Example 5

The lipase of *Mucor javanicus* mentioned above is modified by combining 0.2 g lipase with 1 g pectin A (10% methylated) for 1 h with stirring under nitrogen in an aqueous solution having a pH value of 5. The undissolved pectin is then separated by moderate centrifugation. The solution is then neutralized to pH 7 by addition of a base and is then dried by freeze drying. The milk is subjected to lipolysis by addition of 0.1 U/ml of the modified lipase for 30 minutes at 37° C. and is then dried by spray drying. The lipolyzed powder is used in the production of milk chocolate as described above.

By extraction of the lipid phase of the lipolyzed milk before drying and chromatographic analysis of the free fatty acids, it is found that the modified lipase has the specificity for medium-chain and long-chain fatty acids of the starting lipase and an increased specificity for the unsaturated fatty acids of the same chain length.

Example 6

The milk chocolates produced as described above are subjected to organoleptic evaluation by a panel of tasters immediately after their production (A), after storage for 3 months (B) and after storage for 7 months (C). The following results are obtained:

(A)

The standard chocolate of good quality does not have the flavour of crumb. The chocolate made from the milk powder by the method described above has a crumb flavour to begin with, but very quickly loses this flavour which changes into a very bad odour and taste characteristic of the presence of free short-chain fatty acids. The chocolates of Examples 1, 2, 3, 4 and 5 have a pronounced crumb flavour without producing a bad taste or odour.

(B)

After storage for 3 months, the standard chocolate has a crumb flavour, although not as pronounced as the crumb flavours which the chocolates of Examples 1, 2, 3, 4 and 5 had at the outset. Against all expectations, the chocolates of Examples 1, 2, 3, 4 and 5 do not show an unfavourable development of their organoleptic properties. The product of Example 3 has a finer taste and a better texture than that of Example 4. In addition, the use of lysolecithin (Examples 3 and 4) has the advantage that much smaller quantities of flavouring agent can be used to achieve the desired crumb flavour.

(C)

After storage for 7 months, the chocolates of Examples 1 and 2 have odours appreciably less bad than the standard chocolate.

We claim:

1. A process for preparing a crumb-flavored milk chocolate composition comprising:
   adding free fatty acids to a milk powder, wherein the fatty acids are in a solid state when added to the milk powder and are selected from the group consisting of oleic acid, linoleic acid and α-linolenic acid;
   mixing the milk powder and added fatty acids at a temperature below the melting point of the fatty acids; and
   combining a crumb-flavoring amount of the mixed milk powder and fatty acids with cocoa powder, cocoa butter, sugar and lecithin to obtain a crumb-flavored milk chocolate composition.

2. A process according to claim 1 wherein the free fatty acids are added to the milk powder in an amount of from 0.4% to 1.2% by weight, based upon the weight of the milk powder.

3. A process for preparing a crumb-flavored milk chocolate composition comprising:
   treating a lecithin with phospholipase A2 to obtain a lysolecithin lysate;
   treating the lysate with a protease to inactivate the phospholipase A2 and heating the protease-treated lysate to inactivate the protease; and
   combining a crumb-flavoring amount of the lysate with milk powder, cocoa powder, cocoa butter, sugar and lecithin to obtain a crumb-flavored milk chocolate composition.

4. A process according to claim 3 wherein, based upon the combined weight of the lysate and the lecithin in the milk chocolate composition, the lysate is present in an amount of from 20% to 70% by weight.

5. A process according to claim 4 wherein the lysate is present in an amount of 30% by weight.

6. A process according to claim 4 wherein the lysate is present in an amount of 60% by weight.

7. A process for preparing a crumb-flavored milk chocolate composition comprising:
   incubating a milk with a modified lipase which preferentially releases unsaturated long-chain fatty acids;
   drying the incubated milk to obtain a lipolyzed powder; and
   combining a crumb-flavoring amount of the lipolyzed powder with cocoa powder, cocoa butter, sugar and lecithin to obtain a crumb-flavored milk chocolate composition.

8. A process according to claim 7 wherein the lipase is a pectin-modified lipase.

9. A process according to claim 8 wherein the lipase is a lipase of *Mucor javanicus*.

* * * * *